US00PP10904P

United States Patent [19]

Hansson

[11] Patent Number: Plant 10,904

[45] Date of Patent: May 18, 1999

[54] PETUNIA PLANT NAMED 'REVOLUTION MARROSE'

[75] Inventor: Jorn M. Hansson, Sonderso, Denmark

[73] Assignees: Keisei Rose Nurseries Inc., Tokyo; Suntory Limited, Osaka, both of Japan

[21] Appl. No.: 08/759,670

[22] Filed: Dec. 6, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 6/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |
| P.P. 9,754 | 12/1996 | Suzuki et al. | Plt./68.1 |

*Primary Examiner*—James R. Feyrer

*Attorney, Agent, or Firm*—Burns, Doane, Swecker & Mathis, L.L.P.

[57] ABSTRACT

Disclosed herein is a petunia plant, having a decombent habit plant having long stems. The petunia plant has over-abundant branching and great profusion blooms, the whole bush remaining in bloom for a considerable period of time. The flowers are single, large and bi-color petal with vein pattern, the ground color of bi-colored corolla is strong purplish pink to bright red purple with dark red purple main thick vein pattern and vivid purplish red sub fine vein pattern. The plant has a high resistance to rain, heat, drought, frost and pest.

2 Drawing Sheets

BACKGROUND OF THE VARIETY

The present invention relates to a new and distinct variety of petunia plant obtained from mutant of "Revolution Brilliantpink" obtained from crossing a wild type of petunia plant (♂) native to Brazil and "Recoverer Scarletred (♀)". Such new plant is botanically classified as Petunia x hybrida.

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e., the "Revolution" series [(Revolution Purplepink (U.S. Plant Pat. No. 6,915), Revolution Brilliantpink (U.S. Plant Pat. No. 6,914), Revolution Brilliantpink-mini (U.S. Plant Pat. No. 6,899)] is decumbent type plant having long stems, a lower plant height, abundant branching, and a high resistance to heat, cold and rain. However, there are only a few varieties having a great profusion of flowers, bi-color flower petal and a high resistance to rain, heat, cold and diseases. Accordingly, this invention was aimed at obtaining a new variety having a bi-color flower petal, together with the above features.

The new variety of petunia plant according to this invention originated from mutant occurring as a spontaneously generic variant of "Revolution Brilliantpink" (U.S. Plant Pat. No. 6,914) which we previously filed. The new variety of petunia plant was discovered in view of flower color during propagation of "Revolution Brilliantpink" in May 1993 near Odense, Denmark. The first asexual propagation by cutting took place near Odense, Denmark in November 1993 in a greenhouse operated by Hansson DK. The discovered petunia plant was further propagated by cutting from March, 1994 and then grown in bed and pot on trial from June, 1994 in Denmark and Japan. The botanical characteristics of the plant were examined, using similar variety, "Revolution Brilliantpink", for comparison. As a result, it was concluded that this petunia is distinguishable from any other variety, whose existence is known to us, sufficiently uniform and stable in its characteristics, then this new variety of petunia plant was named "Revolution Marrose".

In the following description, the color-coding is in accordance with The Horticultural Color Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

"Revolution Brilliantpink", the mutant parent of "Revolution Marrose", was obtained from crossing of a new wild type of petunia plant native to Brazil as the pollen parent and "Recoverer Scarletred" as the female parent, in June, 1985 at Yachiyo Farm of Keisei Rose Nurseries, Inc., residing at 755 Owadashinden, Yachiyo-shi, Chiba-ken, Japan.

The female parent use in the breeding of "Revolution Brilliantpink" was a wild type of petunia native to Brazil, the seeds of which were gathered at Gramado, Rio Grande Do Sul, Brazil and introduced to Japan in October, 1983. This wild type of petunia plant is presently maintained at the aforementioned the Yachiyo Farm of Keisei Rose Nurseries, Inc. and the Plant Biotechnology Laboratory of Suntory Ltd., residing at 2913-1 Torihara, Hakushu-cho, Kitakoma-gun, Yamanashi-ken, Japan. The main botanical characteristics of this female parent of "Revolution Brilliantpink" are as follows.

Plant:

*Growth habit.*—Decumbent.

*Plant height.*—20cm.

*Spreading area of plant.*—100–150 cm in diameter.

*Blooming period.*—May to August in the southern Kanto area, Japan.

Stem:

*Length from base.*—50–80 cm.

*Thickness.*—Main stem 2.0–3.0mm; lateral stem 1.5–2.5mm.
*Pubescence.*—Many.
*Branching.*—Over-abundant.
*Length of internode.*—0.1–2.0 cm before blooming; 1.5–3.0 cm during blooming.
*Color.*—Strong yellow green (R.H.S. 144B-144C, J.H.S. 3512-3513).

Leaf:
*Shape.*—Oval.
*Length (average).*—4.5–5.5 cm.
*Width (average).*—2.5–3.5 cm.
*Thickness.*—0.4–0.5 mm
*Color.*—Grayish olive green (R.H.S. 137A- 137B, J.H.S. 3716-3717).
*Phyllotaxis.*—Opposite both before and during blooming.
*Pubescence.*—Few.

Flower:
*Facing direction.*—Opening obliquely upward.
*Type.*—Single.
*Shape.*—Funnel-shape, with five-fissured limb.
*Diameter.*—4.0–5.0 cm.
*Color.*—In the unopened stage (bud), dark reddish purple (R.H.S. 79B, J.H.S. 8907-8909); when open, vivid reddish purple (R.H.S. 74A, J.H.S. 9207), at full bloom, vivid reddish purple (R.H.S. 80A, J.H.S. 8906).
*Reproductive organs.*—1 pistil and 5 stamens, both normal.
*Peduncle.*—0.9–1.2 mm in thickness, and 2.0–2.5 cm in length.

Physiological and ecological characteristics: High resistance to cold, relatively high resistance to heat, and moderate resistance to disease and pest.

"Recoverer Scarletred", used as the female parent in the breeding of variety of "Revolution Brilliantpink", is one of the Recoverer Series bred by the Sakata Seed Corp., Japan. The Recoverer Series includes "Recoverer White", "Recoverer Blue", and "Recoverer Pink", and these plants are commonly characterized by a high resistance to rain. The main botanical characteristics of "Recoverer Scarletred", are as follows.

Plant:
*Growth habit.*—Upright.
*Plant height.*—30–40 cm.
*Spreading area of plant.*—25–35 cm in diameter.
*Blooming period.*—April to September in the southern Kanto area, Japan.

Stem:
*Thickness.*—Main stem 4.5–6.5 mm; lateral stem 2.0–3.0mm.
*Pubescence.*—Normal.
*Branching.*—Abundant
*Length of internode.*—2.0–3.0 cm before blooming; 2.0–4.0 cm during blooming.
*Color.*—Strong yellow green (R.H.S. 144B-144C, J.H.S. 3512-3513).

Leaf:
*Shape.*—Lancet.
*Length (average).*—4.0–5.0 cm.
*Width (average).*—2.0–3.5 cm.
*Thickness.*—0.4–0.6 mm.
*Color.*—Strong yellow green to moderate olive green (R.H.S. 144A-146A, J.H.S. 3507-3508).
*Phyllotaxis.*—Verticillate before blooming; opposite
*Pubescence.*—Few.

Flower:
*Facing direction.*—Opening obliquely upward.
*Type.*—Single.
*Shape.*—Funnel-shape, with five-fissured limb.
*Diameter.*—8.0–8.5 cm.
*Color.*—When flower is open, bright red (R.H.S. 45C 47B, J.H.S. 0407) with moderate pink (R.H.S. 51-C–54C, J.H.S. 0113) reverse side.
*Reproductive organs.*—1 pistil and 5 stamens, both normal.
*Peduncle.*—1.5–2.5 mm in thickness, and 2.5–3.0 cm in length.

Physiological and ecological characteristics: High resistance to rain, heat, and disease, and moderate resistance to pest.

And the botanical characteristics of the petunia plant "Revolution Brilliantpink" which are mutant parent of this new variety "Revolution Marrose" as follows.

Plant:
*Growth habit.*—Decumbent.
*Plant height.*—15–20 cm.
*Spreading area of plant.*—The stem extends to a length of 50–80 cm from the base, and thus the spreading area of the plant is 100–150 cm in diameter.
*Blooming period.*—Late March to Late September in the southern Kanto area, Japan.

Stem:
*Length from base.*—50–80 cm.
*Thickness.*—Main stem 2.5–3.5mm; lateral stem 1.5–2.0mm.
*Pubescence.*—Normal.
*Branching.*—Over-abundant.
*Length of internode.*—1.5–1.7 cm before blooming; 3.0–4.0 cm during blooming.
*Color.*—Strong yellow green (R.H.S. 144A-145A, J.H.S. 3507-3712).

Leaf:
*Shape.*—Lancet.
*Length (average).*—6.0–7.0 cm.
*Width (average).*—2.5–3.5 cm.
*Thickness.*—0.6–0.8mm.
*Color.*—Moderate olive green to strong yellow green (R.H.S. 146A-143A, J.H.S. 3508-3308).
*Phyllotaxis.*—Verticillate before blooming; opposite during blooming.
*Pubescence.*—Few.

Flower:
*Facing direction.*—Opening obliquely upward.
*Type.*—Single.
*Shape.*—Funnel-shape, with five-fissured limb.
*Diameter.*—7.0–8.0 cm.
*Color.*—In the unopened stage (bud), dark reddish purple (R.H.S. 79A-79B, J.H.S. 9516-9210); when open, dark purplish red (R.H.S. 71A, J.H.S. 9509), at full bloom, vivid purplish red (R.H.S. 74A, J.H.S. 9507-9207) with deep reddish purple (R.H.S. 77A, J.H.S. 9209-9210) lines radiating from a dark purple (R.H.S. 83A, J.H.S. 8609-8610) center portion. The reverse side of the petal is a vivid reddish purple color (R.H.S. 74A, J.H.S. 9208-9206). The petal has a metallic luster.

*Reproductive organs.*—1 pistil and 5 stamens, both normal.

*Peduncle.*—1.5–2.0 mm in thickness, and 1.5–2.0 cm in length.

Physiological and ecological characteristics: High resistance to rain, heat and drought. Also high resistance to disease, particularly gray mold (Botrytis). Moderate resistance to pest.

This new and distinct variety of petunia plant, "Revolution Marrose", was asexually reproduced by cutting at the aforementioned Plant Biotechnology Laboratory of Suntory Ltd. and Yachiyo Farm of Keisei Rose Nurseries, Inc., and the homogeneity and stability thereof were confirmed.

SUMMARY OF THE VARIETY

The new variety of petunia plant has bi-color flower petal with vein pattern, and thus is clearly distinguished from a similar variety, "Revolution Brilliantpink", parent of mutant. The plant has decumbent habit, over-abundant branching, especially primary branching is very strong, and great profusion blooms, and the whole bush remains in bloom for a considerable period of time. The flower are single, large and bi-color petal with vein pattern. The ground color of bi-colored corolla is strong purplish pink to bright red purple with dark red purple main thick vein pattern and vivid purplish red sub fine vein pattern. The bottom color of inside surface of the corolla throat is deep purple to dark purple.

The outside color of corolla tube is strong purplish pink. The plant has a high resistance to rain, heat, drought, frost and pest.

DESCRIPTION OF THE VARIETY

Figure 1:
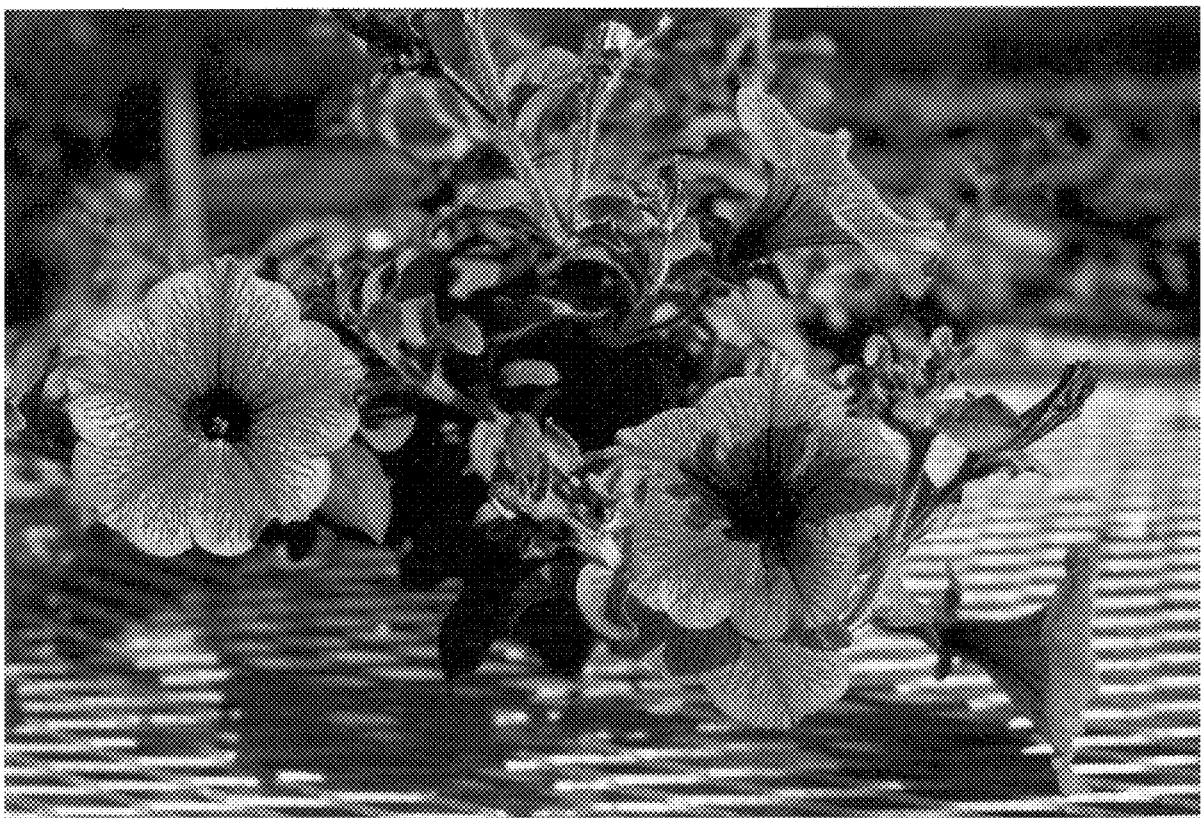
FIG. 1 is a photograph giving a partial view of the new variety of petunia plant planted in a flower pot.
Figure 2:
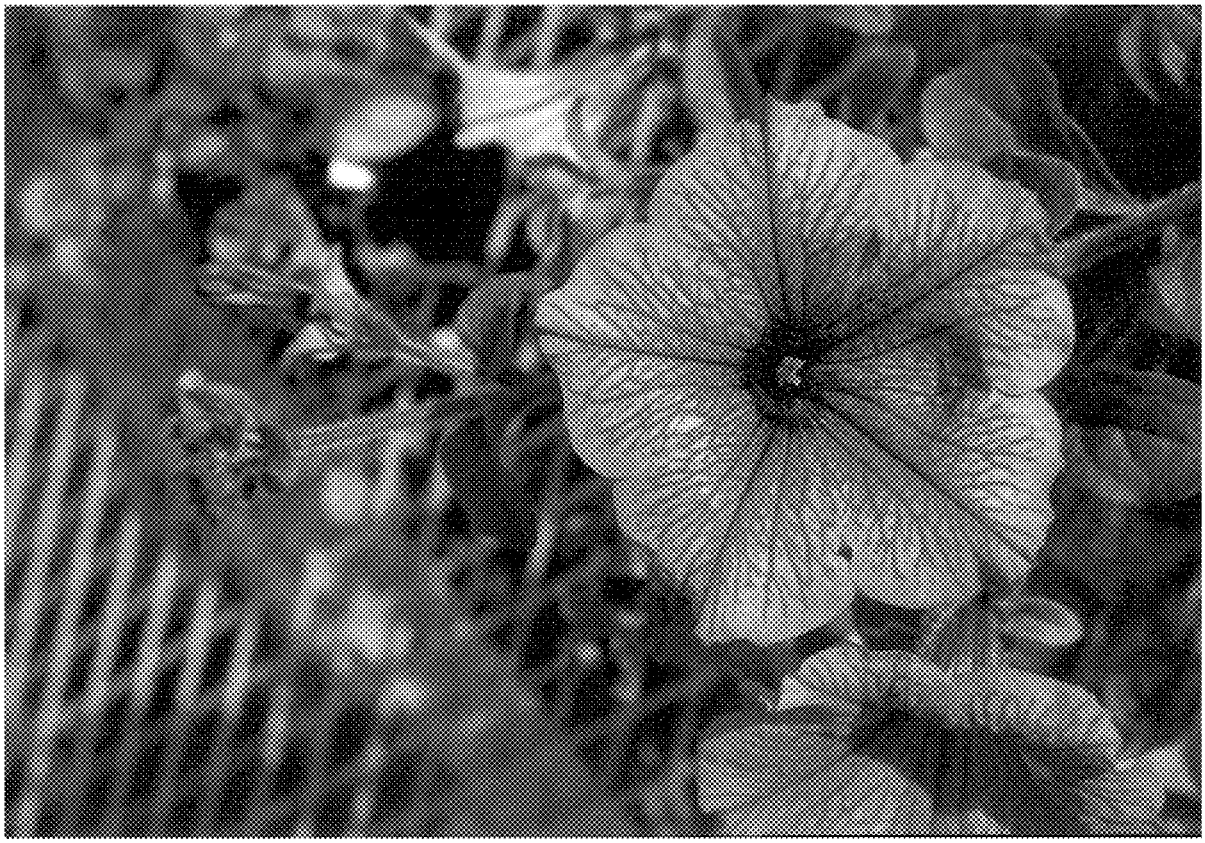
FIG. 2 is a photograph of flowers of the new variety of petunia plant.

The botanical characteristics of the new and distinct variety of petunia plant "Revolution Marrose" are as follows.

Plant:

*Growth habit.*—Decumbent. The stems hang down when potted in a hanging pot.

*Plant height.*—15–21 cm.

*Spreading area of plant.*—The stem extends to length of 50–80 cm from the base, and thus the spreading area of the plant is 110–150 cm in diameter.

*Growth.*—Very vigorous with abundant branching, a great profusion of blooms; the whole bush remaining in bloom for a considerable this period of time.

*Blooming period.*—Late March to early October in the southern Kanto area, Japan. The plant shape does not change throughout this period.

Stem:

*Thickness.*—3.0–4.5 mm.

*Pubescence.*—Normal.

*Branching.*—Over-abundant, especially primary branching is very strong.

*Length of internode.*—3.0–5.5 cm.

*Color.*—Dark yellow green to deep yellow green (R.H.S. 144A-146A, J.H.S. 3507-3508).

Leaf:

*Shape.*—Lanceolate.

*Length.*—4.0–6.0 cm.

*Width.*—2.5–4.0 cm.

*Thickness.*—0.5–0.7mm.

*Color.*—Dark yellow green to strong yellow green (R.H.S. 146A-145A, J.H.S. 3508-3512).

*Phyllotaxis.*—Verticillate before blooming; opposite during blooming.

*Pubescence.*—Normal.

Flower:

*Facing direction.*—Opening obliquely upward.

*Type.*—Single.

*Shape.*—Funnel-shape, with five-fissured limb.

*Waving grade of petal.*—Week.

*Lobation of petal.*—*Medium.*

*Shape of petal tip.*—Acute.

*Diameter.*—6.5–8.0 cm.

*Petal.*—Bi-color of the corolla and variegated pattern of bi-color corolla is vein.

*Color.*—Ground color of bi-colored corolla is strong purplish pink to bright red purple (R.H.S. 61D-63B, J.H.S. 9505-9506) with dark red purple (R.H.S.79B, J.H.S. 9210) main thick vein pattern and vivid purplish red (R.H.S.57C, J.H.S. 9707) sub fine vein pattern. The bottom color of inside surface of the corolla throat is deep purple to dark purple (R.H.S.86A, J.H.S. 8608-8609).

The outside color of corolla tube is strong purplish pink (R.H.S.61D, J.H.S. 9505).

*Reproductive organs.*—1 normal pistil and 5 normal stamens. 2 stamens are higher the pistil).

Physiological and ecological characteristics: High resistance to rain, heat, drought, frost and pest.

This new variety of petunia plant is most suitable for flower bedding and potting, particularly in hanging pots or planters, and further excellent for ground cover.

The plant of this new variety "Revolution Marrose" is presently planted and maintained at the Plant Biotechnology Laboratory of Suntory Ltd., residing at 2913-1 Torihara, Hakushu-cho, Kitakoma-gun, Yamanashi-ken, Japan, and at the Yachiyo Farm of Keisei Rose Nurseries, Inc., residing at 755 Owadashinden, Yachiyo-shi, Chiba-ken, Japan.

I claim:

1. A new and distinct variety of petunia plant, substantially as herein illustrated and described, characterized particularly as to novelty by (A) being a decumbent habit plant having long stems, (B) an over-abundant branching and great profusion blooms, the whole bush remaining in bloom for a considerable period of time, (C) flowers are single, large and bi-color petal with vein pattern, the ground color ob bi-colored corolla is strong purplish pink to bright red purple with dark red purple main thick vein pattern and vivid purplish red sub fine vein pattern, (D) a high resistance to rain, heat, drought, frost and pest.

* * * * *

REVOLUTION 'MARROSE'

REVOLUTION 'MARROSE'